(12) United States Patent
Giller et al.

(10) Patent No.: US 6,567,690 B2
(45) Date of Patent: May 20, 2003

(54) METHOD AND APPARATUS FOR PROBE LOCALIZATION IN BRAIN MATTER

(76) Inventors: Cole Giller, 6408 Duffield, Dallas, TX (US) 75248; Hanli Liu, 706 Gunnison Ct., Arlington, TX (US) 76006

( * ) Notice: Subject to any disclaimer, the term of this patent is extended or adjusted under 35 U.S.C. 154(b) by 0 days.

(21) Appl. No.: 09/847,997

(22) Filed: May 3, 2001

(65) Prior Publication Data

US 2002/0045832 A1 Apr. 18, 2002

Related U.S. Application Data

(60) Provisional application No. 60/240,690, filed on Oct. 16, 2000.

(51) Int. Cl.$^7$ .................................................. A61B 6/00
(52) U.S. Cl. ....................... 600/473; 600/424; 600/478; 128/898
(58) Field of Search ................................ 600/473, 424, 600/478; 128/898

(56) References Cited

U.S. PATENT DOCUMENTS

| | | | | |
|---|---|---|---|---|
| 5,713,364 A | * | 2/1998 | DeBaryshe et al. | 128/664 |
| 5,803,082 A | * | 9/1998 | Stapleton et al. | 128/653.1 |
| 5,845,639 A | * | 12/1998 | Hochman et al. | 128/653.1 |
| 6,413,084 B1 | * | 7/2002 | Rubbert et al. | 433/29 |

OTHER PUBLICATIONS

"Impedance Method for Localizing Brain Structures"; B. Robinson and H. Tompkins; Archives of Neurology, vol. 10; 1964.

"Locating Brain Structures, Extensions in Impedance Method"; Bryan W. Robinson, James S. Bryan and H. Enger Rosvold; Arch Neuro– vol. 13; Nov. 1965.

"The Value of Impedance Measurements to Aid in the Localisation in Stereotactic Surgery"; G. Dierseen and E. Marg; 2nd Symp. Stereoencephalotomy, Copenhagen, 1965.

"Impedance and Phase Angle as a Locating Method in Human Stereotaxic Surgery"; Lauri Laitinen, Gunnar Johansson and Pentti Sipponen; Neurological Clinic, University Central Hospital, Helsinki, Finland.

"Tissue Impedance Along Probe Trajectories in Thalamotomy"; J. Aguilar, S. Tachibana and L. Birzis; 4th Symp. Int. Soc. Res. Stereoencephalotomy, New York, 1970.

* cited by examiner

Primary Examiner—Marvin M. Lateef
Assistant Examiner—Devaang Shah
(74) Attorney, Agent, or Firm—Howison, Thoma & Arnott, L.L.P.

(57) ABSTRACT

Method and apparatus for probe localization in brain matter. A method is disclosed for determining the insertion point for an object at a desired location within tissue of varying types. The parameters of tissue are first measured at an entry point into the tissue from exterior thereof. The parameters of the tissue are then measured periodically along a line extending from the entry point and moving away therefrom. A determination is then made if at least one boundary between tissue types has occurred during the measurement process. The measurements along the line are then compared to a predetermined map of the tissue boundaries. Thereafter, a point on the map is then selected corresponding to the desired location within the tissue when the measured parameters indicate that the measurements are taking place in proximity thereto.

13 Claims, 7 Drawing Sheets

METHOD AND APPARATUS FOR PROBE LOCALIZATION IN BRAIN MATTER

CROSS REFERENCE TO RELATED APPLICATIONS

This application claims priority to Provisional Application Ser. No. 60/240,690, filed Oct. 16, 2000.

TECHNICAL FIELD OF THE INVENTION

This invention is related to implantable probes in the medical industry and, more particularly, to a method for assisting in the implant of a probe.

BACKGROUND OF THE INVENTION

Although the small subcortical structures targeted during placement of deep brain stimulation (DBS) electrodes can often be visualized on CT or MRI images, the use of imaging alone to guide stereotactic placement is generally considered to be inadequate. CT scans do not clearly visualize important targets such as the internal segment of the globus pallidus in the brain, and do not permit direct use of key coronal planes. MRI images show exquisite anatomic detail, but the effects of magnetic field inhomogeneities, varying magnetic susceptibility, and chemical shifts combine to distort the image and make its stereotactic accuracy uncertain. Although methods have been advocated to minimize MRJ distortion, none have been proven to eliminate all of these difficulties in all conditions. These factors, together with individual anatomic variations, result in the belief of most centers that some form of intraoperative localization is crucial to augment the information derived from imaging.

One of the oldest and most accepted methods of intraoperative localization is that of stimulation, in which the clinical effects of electrical current passed through a test electrode are used to guide position. For example, the proper position for thalamotomy is 1 to 2 mm anterior to a site where stimulation invokes facial and hand response. The accuracy attainable by stimulation is limited, however, by variations in the amount of current spread, differences in individual responses and the inability to accurately measure distances to nearby activated structures.

Electrical impedance has also been used to detect boundaries of subcortical structures. The reported resolution in animal models was excellent but required use of a sharp needle-like probe and electrical shielding. Subsequent use in humans used probes with a more blunt probe tip profile, but these were believed to have less spatial resolution. Although a few clinicians continue to use impedance for intraoperative localization, most centers have abandoned this technique.

Such dissatisfaction for small targets led to development of microelectrode recording (MER), first introduced in humans by Albe-Fessard. In these methods, the specific electrical signals of single neurons, or groups of neurons, are recorded with a fine-wire electrode and used to create an anatomic and physiologic map of key subcortical structures. MER allows definition of important small subcortical nuclei as well as the fine white matter laminae surrounding them. This technique is considered essential by some investigators, and has been used for almost 30 years for reliable and detailed intraoperative guidance.

MER provides two types of information. The first is the identification of areas specific to sensorimotor function (as in globus pallidus targeting) or specific nuclei. The second is the identification of the anatomic extent of the target structure either by mapping the extent of its specific "neuronal signature" or by identifying adjacent boundary structures such as the internal capsule and optic tract. Since most stereotactic targets consist of gray matter surrounded by laminae of white matter, this latter use of MER has been universally used in all centers using MER. For example, one article recently reported the ease and speed of their MER protocol, which emphasized identification of white matter boundaries inferior and medial to the pallidum and dimensions of globus pallidus subcomponents.

There is nevertheless considerable debate regarding the necessity, risks and costs of MER. The requirement of specialized equipment and expertise in neurophysiology adds cost and complexity, while the necessity for painstaking recordings every few microns along tracks several centimeters in length adds time to the procedure, and possibly stress to the awake patient. Several probe tracks are thought necessary to properly use MER adding to the risk of catastrophic hemorrhage, which increases slightly with each track. If DBS placement is believed to be unacceptable without MER, these difficulties may severely limit public access to DBS outside of a few major centers.

While many centers strongly advocate MER, others have questioned the necessity of MER to obtain appropriate clinical results, and MER is not used by the same center that reintroduced pallidotomy into the modern era. Furthermore, a number of groups have reported good results of pallidotomy performed without MER. One group found a 46% improvement in UPDRS motor scores at 12 months following pallidotomy without MER. Another showed a 30% improvement in off-state UPDRS motor scores in their cohort of patients 12 months following pallidotomy without MER. Yet another showed a 44% improvement in off-state UPDRS motor scores after pallidotomy without MER, although the follow-up time was only 3 months. A further one, however, reported five pallidotomies without MER with no improvement. This poor outcome may be due to this report being based upon their early experience, and the use of MRI images without anatomic compensation. These results without MER compare favorably with results of some researchers, which showed clinical improvements of 15, 21, 30 and 30.1%, respectively, at 6 or 12 months after pallidotomy with MER. The improvement in mean off-state UPDRS scores of 58.6% twelve months following pallidotomy with MER is higher than found by most centers.

The need for MER during thalamic procedures has also been questioned, and some centers using MER for pallidotomy do not use this technique during thalamotomy. Furthermore, although localization of the subthalamic nucleus (STN) is achieved my most centers with MER, the ease by which STN is visualized on MRI is cause to question the necessity of MER in this setting.

Whether the use of MER significantly improves clinical results remains controversial. The studies above suggest that the full complement of information available from MER may not be required. This is further supported by the emphasis some centers give to the use of MER to identify gray-white junctions rather than provide detailed maps of neuronal signatures.

MER recordings are typically made by slowly inserting the microelectrode by micrometer increments over a distance of 2 to 3 cm. Each neuron is tested for response to cutaneous stimuli, active and passive limb movements, as well as for its neuronal signature. Such exhaustive testing can take several hours per track and since most protocols require several tracks, most centers use abbreviated protocols to avoid an enormous time requirement. Although typical track times are 30 to 60 minutes, the shortest time per track that has been reported is 20 to 30 minutes. However, after several tracks, even these short protocols add an hour or more to the surgical procedure. Furthermore, these short protocols do not utilize all the data available from MER, and emphasize the identification of gray-white boundaries that might also be obtained from less awkward modalities. Finally, the reports of shorter protocols are from institutions with experience with MER under ideal circumstances. Since MER in practice is quite difficult (factors include fragile probes, the hostile electrical environment of the operating room and the complexity of the recording equipment), it is unlikely that these ideal times can be duplicated by most centers. MER therefore remains a difficult technique that can add significant time to stereotactic procedures.

The amount of risk associated with MER is controversial. Although each extra track adds some risk of hemorrhage, the probability of hemorrhage per track is debated. Several experienced centers have reported low rates of 1 to 2% of hemorrhagic complications. Other groups have not been as fortunate, reporting severe hemorrhage rates of 7%. The discrepancy between these rates from groups early in their experience with the lower rates from more established centers suggests that the risk of MER is real but decreases with experience. Whether the risk of MER attained by these few exceptional centers were matched by the majority of centers performing DBS is debatable.

An explanation for the risk associated with MER is the sharp tip profile of the microelectrode. As noted by one researcher, the blunt tip profile of the NMR probe may confer added safety when compared to sharp electrodes such as used in MER. In primate data from a single laboratory, these investigators reported two intracranial hemorrhages in 60 sharp electrode tracks, while hemorrhages were never encountered in more than 350 electrode tracks with blunt electrodes.

Commercially available systems for MER cost about $100,000. Although systems can be assembled less expensively from individual components, the requirements of high impedance amplification and of a microdrive capable of micrometer increments cannot be avoided. In addition to the technical assistance required to maintain and run the MER recording equipment, interpretation of single cell recording requires neurophysiological expertise. Most centers have found the presence of a trained neurophysiologist in the operating room to be essential, adding to the overall cost.

Probes with sensors mounted at their tip can only "look ahead" to interrogate tissue in the probe path. However, the ability to detect gray-white differences perpendicular to the probe path would be invaluable in clinical practice. For example, to ensure adequate proximity to the internal capsule during placement of a thalamic deep brain stimulator electrode, it is often necessary to create a second, more lateral track to map the position of the capsule. If, however, the white matter of the capsule could be detected perpendicular to the original track with a side looking probe, then the proximity of the capsule could be so confirmed and the need for an additional track (with additional morbidity) could be obviated. Current methods of MER are not capable of interrogation perpendicular to the probe axis since the electrodes are straight and cannot be bent.

SUMMARY OF THE INVENTION

The present invention disclosed and claimed herein comprises, in one aspect thereof, a method for determining the insertion point for an object at a desired location within tissue of varying types. The parameters of tissue are first measured at an entry point into the tissue from exterior thereof. The parameters of the tissue are then measured periodically along a line extending from the entry point and moving away therefrom. A determination is then made if at least one boundary between tissue types has occurred during the measurement process. The measurements along the line are then compared to a predetermined map of the tissue boundaries. Thereafter, a point on the map is then selected corresponding to the desired location within the tissue when the measured parameters indicate that the measurements are taking place in proximity thereto.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

NIR Reflectance

Figure 1:
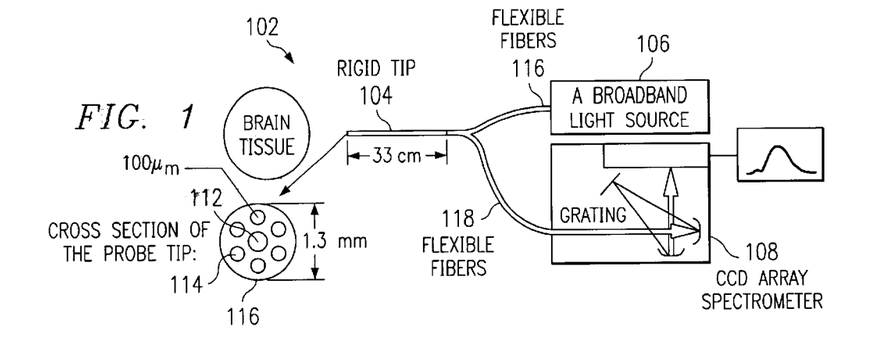
FIG. 1 illustrates an NIR instrument with a broadband light source, a charged coupled device (CCD) spectrometer, and a custom-designed stereotactic probe.

Referring now to FIG. 1, there is illustrated an NIR spectroscopic system with a probe 104 designed to measure brain tissue reflectance during stereotactic procedures in humans to distinguish gray and white matter. This is described in Johns, 1997, Johns et al and 1998; Giller et al, 1998, all of which are incorporated herein by reference. The basic instrumentation for such reflectance measurement from tissue includes a broadband light source 106, a portable, real-time display spectrometer 108 (S2000, Ocean Optics, Inc.), and a fiber optic probe 110.

As shown in FIG. 1, the probe 110 consists of a single NIR emitter fiber 112 surrounded by six detector fibers 114, housed in a probe of similar dimensions to those already used in stereotactic procedures. The fiber optic probe 110 measured three meters in total length. The first 33-cm of the probe is fabricated of hypoallergenic stainless steel, and the remaining length of the fiber bifurcated into two one-meter segments 116 and 118. The segment 116 is connected to the light source 106, a tungsten-halogen light source, and the other segment 118 to the spectrometer 108 which was grated for wavelengths between 350 and 850 nm. All fibers 112 and 114 are 100-m in diameter with a core-to-core separation of approximately 150-mm. This configuration prevents the detectors from being saturated based on results obtained from laboratory model studies. With a 150 m core-to-core separation, detection of tissue can be facilitated extending 50–100 micrometers beyond the probe tip 116.

Figure 2A:
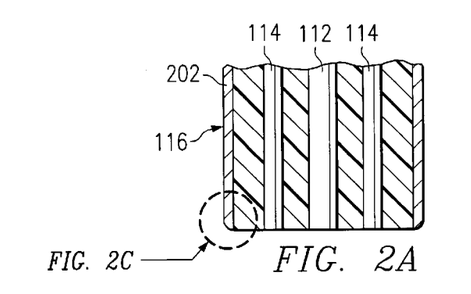
FIGS. 2a–2c illustrate various views of the probe.
Figure 2B:
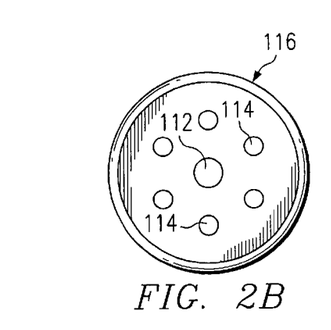
Figure 2C:
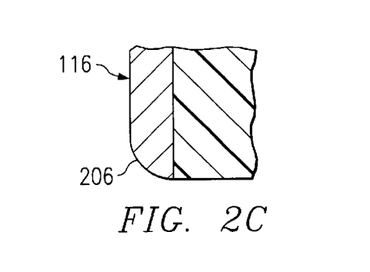

Referring now to FIGS. 2a–2b, there are illustrated various views of the probe 116. The probe 116 has a metal sheath 202 with the fibers 112 and 114 disposed therein. There are illustrated two of the receive fibers 114 and the single center transmission fiber 112. The fibers 112 and 114 are disposed within the sheath and encased therein with a "potting" compound such as a resin of the sort utilized to hold fibers in place. They are each approximately 100 microns in diameter and separated from each other by a distance of approximately 150 microns. An end view of the probe is illustrated in FIG. 2b. FIG. 2c illustrates a detail of the corner at the end of the probe 116. It can be seen that the end of the metal sheath 202 proximate to the corner has a rounded edge 206 that allows for easy and safe insertion, as opposed to a sharp corner. A round corner such as the rounded edge 206 is associated with less tissue injury than a sharp corner.

Figure 3:
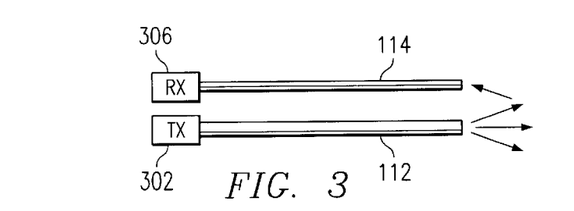
FIG. 3 illustrates a side view of the probe illustrating the transmission and reception properties.

Referring now to FIG. 3, there is illustrated a diagram of each of the receive fibers 114 (illustrating only one) and a transmission fiber 112. The transmission fiber 112 is illustrated as a separate fiber that is operable to receive light at a defined wavelength from a transmission device 302, which comprises the broadband light source 106 of FIG. 1. This is operable to transmit light to the fiber 112 which is emitted from the end thereof. The receive fibers 114 are operable to receive reflections of the light from the surrounding tissue and transmitted along the fiber 114 back to a receiver 306, which is the CCD array spectrometer 108. The number of receive fibers 114 that are required is dependent upon the sensitivity of the receiver 306. The fibers 114 primarily perform a "collection" operation of the light.

Figure 4:
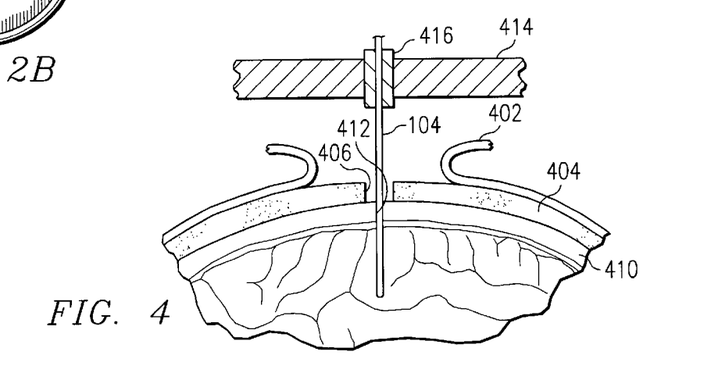
FIG. 4 illustrates the insertion operation of the probe.

Referring now to FIG. 4, there is illustrated a side view of the technique for inserting the probe 104 into the brain. Initially, an opening is formed by separating the scalp 402 from the bone 404. An opening 406 is formed in the skull to expose the dura layer 410. A hole 412 in the dura layer 410 is then made to expose the brain tissue. A stabilized mounting device 414 is provided that has a guide 416 associated therewith. This guide is tubular in nature such that the probe 104 can be inserted therein and the guide 416 will maintain stability of the probe 104 as it is moved along its longitudinal axis. The guide 416 is provided to allow the probe 104 to be inserted into the brain and disposed a predetermined distance thereto. Thereafter, the probe 104 can be removed and then, possibly, a diagnostic device such as a mnicroelectrode or other device inserted through the guide 416 down to a depth determined through the reflectance and insertion procedure, as will be described hereinbelow. This diagnostic device could be a microelectrode for providing stimulus or it could even be utilized for disposing a therapeutic device or drug at a desired location within the brain tissue.

Figure 5:
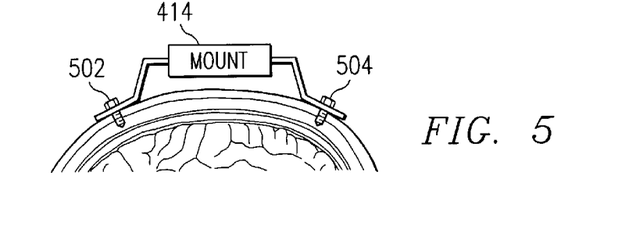
FIG. 5 illustrates the mount for inserting the probe.

Referring now to FIG. 5, there is illustrated a diagram of the mount 414 and the manner by which it is attached to the skull. This mount is attached to the skull with mounting screws 502 and 504. The mount 414 is associated with a CRW or other type of stereotactic frame. The screws 504 are secured to the skull and require approximately a 2 mm penetration to provide securing thereto. The mount 414, although illustrated in FIG. 4 as having a fixed guide 416, could be more complicated and have a moveable guide that would vary the angle of insertion without requiring the screws 502 and 504 to be moved to a different location. Alternatively, the probe may be advanced freehand using a frameless stereotactic device.

Figure 6:
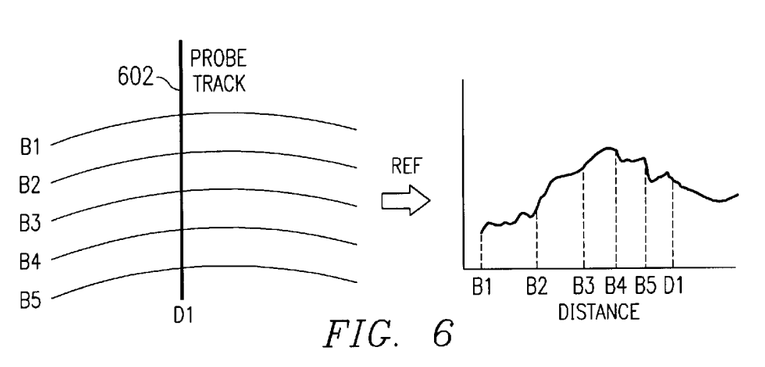
FIG. 6 illustrates the mapping of function as the probe traverses boundaries.

Referring now to FIG. 6, there is illustrated a diagram of the mapping operation. In FIG. 6, there is provided a probe track 602 which defines the path that is traversed by the probe 104 through the brain tissue. As the probe traverses the tissue, it measures the reflectance from the surrounding tissue. By correctly analyzing this reflectance and the difference of the reflectance between successive sites of measurements, a determination can be made as to when a boundary is encountered, the boundary being the differentiation between tissues. These are illustrated as boundaries B1, B2, B3, B4 and B5. These are illustrated as very uniform boundaries, although it should be understood that boundaries of various tissue types in the brain are anything but uniform. These boundary sites can then be compared to those seen in imaging studies such as MRI and CT to identify sites of particular structure.

The path 602 that the probe traverses is linear in nature and is operable to terminate at a destination D1. For example, it may be desirable to insert the probe into a defined location in the brain. By recognizing that the boundary B5 has been traversed, then it is known that the region in which destination D1 resides has been reached. It may be that the probe would be required to go through boundary B5 to another boundary, which is the opposite boundary (not shown) to that associated with D1, thus defining the boundaries of the region associated with D1. Once these boundaries can be determined, then the probe can be moved to the proper location. This might be a finite distance past the boundary B5 or midway between the opposite boundary (not shown) for the region associated with destination D1.

The traversal of the path 602 by the probe is illustrated in a graph of reflectance v. distance. As the reflectance parameters change at the boundaries, the determination can be made that a boundary has been reached. With knowledge of the brain anatomy, the traversal path 602 can be compared to a brain map such as provided by studies such as MRI and CT and the various locations that have been traversed determined. It is these defined boundaries that allow the operator to know approximately at what location the probe finally rests. Since the brain map is generally known, a general idea of where the boundaries are is something that is known. However, during the procedure, it is not uncommon that the brain would "collapse" or "sag" somewhat, thus modifying the map. However, once the "profile" as defined by the traversal of the path 602 is measured, this can be compared to expected results and the operator actually be provided with a graphical view of how the path is being traversed in a simulated brain.

The matching process between the boundaries determined by the infrared probe and the anatomic map (such as MRI or CT) can be further quantified as follows. The collection of all possible probe paths can be computed as a collection of straight lines in 3-dimensional space, and the reflectance data associated to each of these paths can be approximated from the gray scale information inherent in the anatomic map. The measured reflectance from the actual probe path can then be compared to the calculated reflectance data for each of the calculated paths, and the calculated path having reflectance closest to that of the actual path can be chosen using standard optimization techniques (e.g., least squares). This chosen calculated path thereby provides the best estimate of the exact anatomic position of the actual path taken by the infrared probe.

Figure 7:
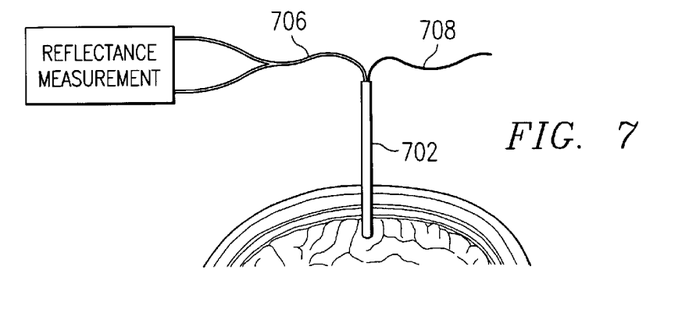
FIG. 7 illustrates an alternate combined probe/microelectrode.
Figure 7A:
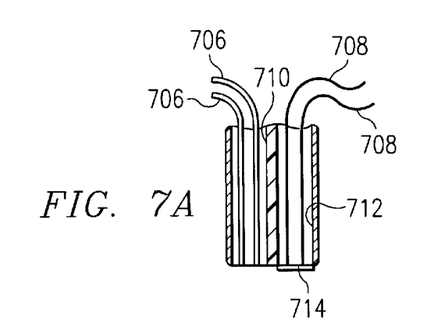
FIG. 7a illustrates in detail the probe of FIG. 7.

Referring now to FIG. 7, there is illustrated a diagrammatic view of an alternate probe. This is illustrated as a probe 702, which is similar to the probe 104 in that it is a rigid device with a metal sheath. However, this probe 702 facilitates containing both transmit and receive fibers 706, similar to the fibers 112 and 114 of FIG. 1, and also receives electrode wires 708. The electrode wires 708 are operable to interface with a diagnostic device such as an electrode that can be disposed at the end of the probe over the length thereof. A detail of this is illustrated in FIG. 7a. There is provided a canal 710 through which the fibers 706 are passed. As was the case described hereinabove, these fibers 706 would constitute a transmit fiber and one or more receive fibers that would be secured therein with some type of resin or potting compound. Similarly, there is provided a second canal 712 having disposed therein proximate to the end of the probe a microelectrode 714, for example. The electrode wire 708 associated therewith would extend upward through the canal 712. In this manner, the probe facilitates both location and diagnostic or therapeutic benefits.

Figure 8:
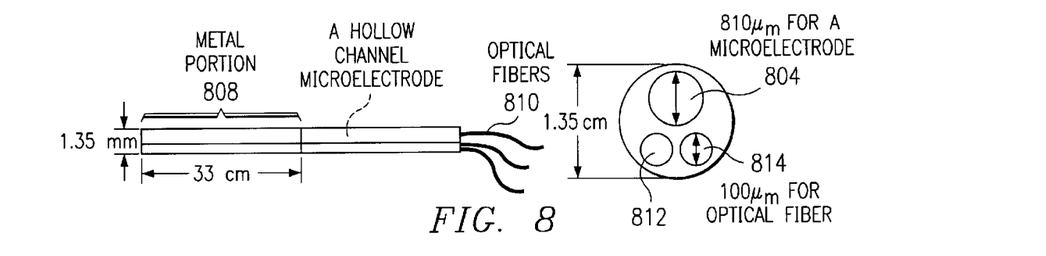
FIG. 8 illustrates an alternate embodiment of the probe configuration.

Referring now to FIG. 8, there is illustrated a view of a probe configuration with a hollow channel for the microcore. The probe is comprised of a rigid metal portion 808 of approximately 33 cm in length which has disposed in there a hollow channel 804. The hollow channel runs along the length thereof to allow microelectrodes 810 to be disposed therein. The diameter of the probe is approximately 1.35 mm wherein the channel for the microelectrode is approximately 810 microns. There are provided two channels 812 and 814 for the optical fiber. These are 100 microns in diameter.

Figure 9:
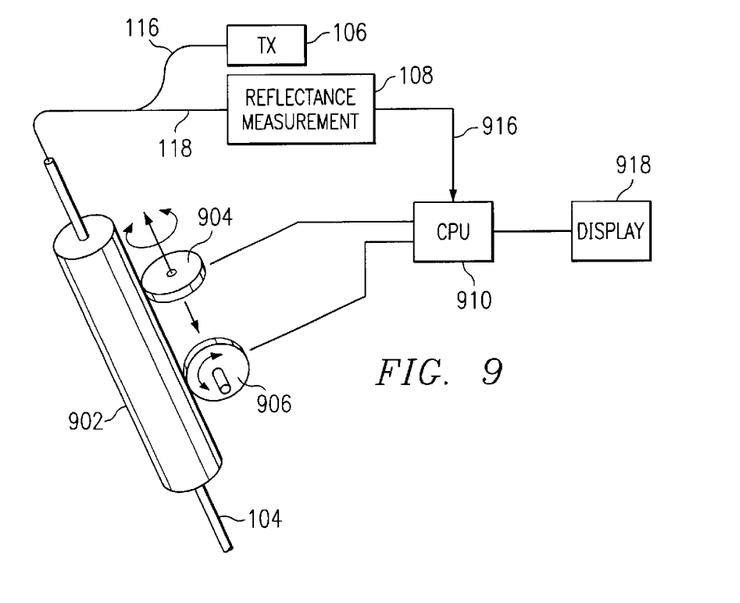
FIG. 9 illustrates a diagrammatic view of automatic probe insertion.

Referring now to FIG. 9, there is illustrated a diagrammatic view of an alternate embodiment for automatically inserting the probe 104. The rigid portion of the probe 104 is disposed within a holder 902 which is cylindrical in shape and has a central longitudinal cavity disposed therethrough for holding the probe 104. The probe 104 is held such that it is secured within the holder 902, such that when the holder 902 is reciprocated along its longitudinal axis or rotated about its longitudinal axis, the probe 104 will track these movements. In general, the holder 902 is cylindrical in shape such that it can be rotated with a driving wheel 904 which is driven with a servo motor (not shown). The longitudinal movement is driven with a rotating wheel 906 that has a direction of rotation perpendicular to the longitudinal axis. The wheel 906 is driven with a servo motor (not shown). Each of the wheels 904 and 906 have their servo motors driven by control signals that are received from a CPU 910. Therefore, the probe can be moved in an incremental or a linear manner such that a reflection measurement can be taken and transmitted back along the flexible transmit and receive fibers. The reflectance measurement device 108 is the CCD array spectrometer. This provides an output to the CPU on a line 916. Therefore, the CPU 910 can utilize the output of the CCD array spectrometer 108 to determine if further longitudinal travel is required. The rotational aspect thereof will be described hereinbelow with respect to a "side-looking" probe. The CPU 910 is operable to output the results thereof on a display 918.

Figure 10:
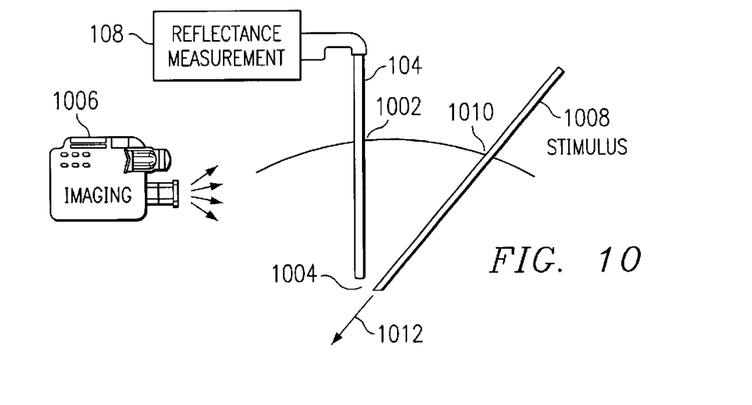
FIG. 10 illustrates a diagrammatic view of a method for inserting a device utilizing the probe as a locating device.

Referring now to FIG. 10, there is illustrated a method for locating a desired destination in the brain tissue (or any other tissue) and then directing another stimulus or diagnostic probe to the location from a different angle and at a different insertion point. The probe 104 is inserted into the tissue at a location 1002. Using the reflectance measurement CCD array spectrometer 108, the probe tip can be inserted to a location 1004 within the tissue, this being the desired location. An imaging or other stereotactic device 1006 is then used to determine the location of the probe in three dimensions. This can be any type of conventional imaging device. Thereafter, a stimulus/diagnostic probe 1008 can be inserted at a different location 1010 on the surface of the tissue and then pushed through the tissue on a path 1012 such that the tip thereof arrives at the location 1004. This allows the probe 104 to be utilized for location and maintained in that location until the probe 1008 is inserted therein. This accounts for any type of movement that may occur during insertion of the probe 1008. For example, if the probe 104 were removed and then the probe 1008 inserted into the same location along the same path, any movement of the tissue or deviation from the original path would be unrecognized and the operator is proceeding "blind."

Figure 11:
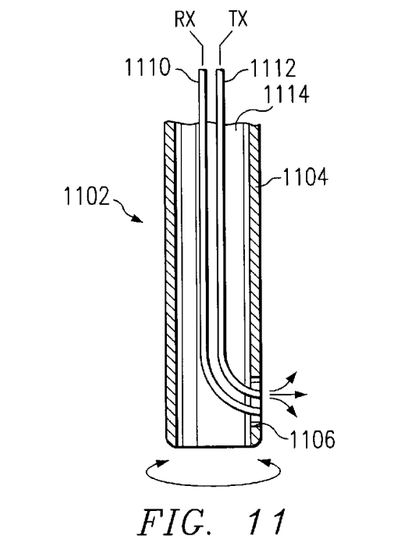
FIGS. 11–12 and 12a illustrate alternate embodiments for a side-probe.

Referring now to FIG. 11, there is illustrated an alternate embodiment of the probe 104. This is illustrated as a probe tip 102 which is, as described hereinabove, a rigid member having a cylindrical outer shell 1104 with an orifice 1106 disposed therein. The interior of the shell 1104 contains both a receive fiber 1110 and a transmit fiber 1112 that traverse the interior of the probe tip 1102 along the longitudinal axis thereof. However, at the lower end thereof, both the receive fiber 1110 and the transmit fiber 1112 have a right angle associated therewith such that they exit the orifice 1106. Thereafter, an interior compound 1114 is provided to secure the fibers 1110 and 1112 within the interior of the shell 1104.

Figure 12:
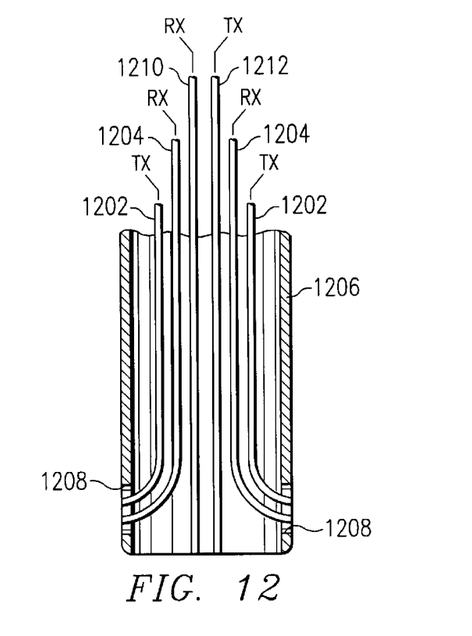
Figure 12A:
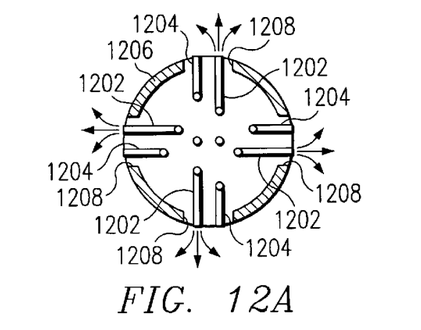

Referring now to FIG. 12, there is illustrated an alternate embodiment of FIG. 11. This probe utilizes a plurality of transmit fibers 1202 and receive fibers 1204 that are disposed within the interior of a cylindrical shell 1206. There are provided a plurality of orifices 1208 through which the ends of the fibers 1202 and 1204 can extend, these orifices disposed in the lower side wall of the probe tip, as was the case with the probe of FIG. 11. Each of the probes of FIG. 11 and FIG. 12 are operable to rotate in order to determine the reflectance in the local area associated therewith. Additionally, there are provided two center fibers, a receive fiber 1210 and a transmit fiber 1212 that are operable to extend out to the end of the probes such that they are directed along the longitudinal axis. With the probe tip of FIG. 12, both side looking and in looking can be provided at multiple angles. A cross section of the embodiment of FIG. 12 as illustrated in FIG. 12a, illustrating that the openings as being directed in four different side-looking directions.

Figure 13:
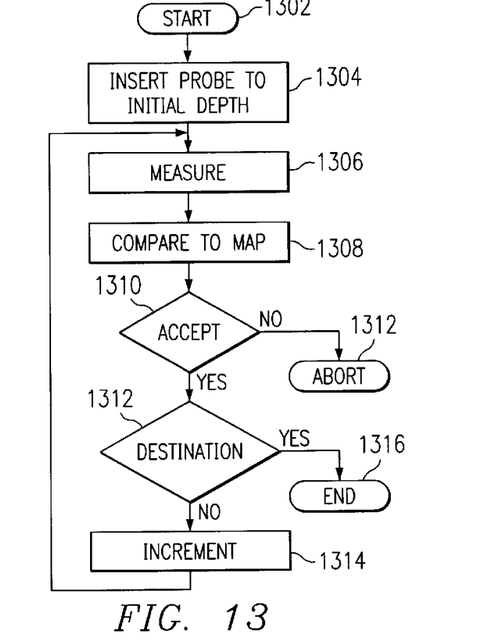
FIG. 13 illustrates a flow chart depicting the operation of inserting the probe and comparing it to a map.

Referring now to FIG. 13, there is illustrated a flow chart depicting the overall operation of inserting the probe for an automatic operation. The program is initiated at a start block 1302 and then proceeds to a function block 1304 wherein the probe is inserted to an initial depth. Although a linear operation could be utilized, the probe must be started at a finite point. A measurement is then taken, as indicated by function block 1306 then the program proceeds to function block 1308 to compare the measurement to a predetermined map or desired path, as described hereinabove. The program then flows to a decision block 1310 to determine if the measurement along this path is acceptable, i.e., the probe is traversing the correct path and the results are as expected. If the results are not acceptable, i.e., it has veered off the correct path, the program will abort, as indicated by a block 1312. However, if it is an acceptable measurement, i.e., the probe is traversing the correct path, the program will flow to a decision block 1312 wherein it is determined whether the probe is at the destination, i.e., it has traversed the full length of the desired path. If not, the program will flow along a "N" path to a function block 1314 to increment the probe along the path by a finite amount. The program will then flow back to the input of function block 1306 to make the measurement. When the destination has been arrived, the program will flow along the "Y" path from the destination decision block 1312 over to an End block 1316. Alternative to the increment operation, measurements could be taken along the entire path and then an algorithm utilized to determine where the destination is using all data.

In vitro Measurements

The initial in vitro measurements, in one application of the disclosed device, were performed using liquid tissue models with different scattering and absorption properties. The liquid phantom model was made of a mixture of Intralipid (a turbid suspension of fat particles with various dye solutions.) Various concentrations of Intralipid and dye provide different scattering and absorption properties, respectively, for the tissue model The data clearly showed that the optical reflectance increases as absorption in the liquid phantom increases, whereas the reflectance increases in proportion to the increase of scattering of the phantom. This result is in good agreement with the theoretical expectation and confirms the ability of the NIR probe to distinguish materials with different scattering and absorptive properties.

Measurements from Lobectomies

Figure 14:
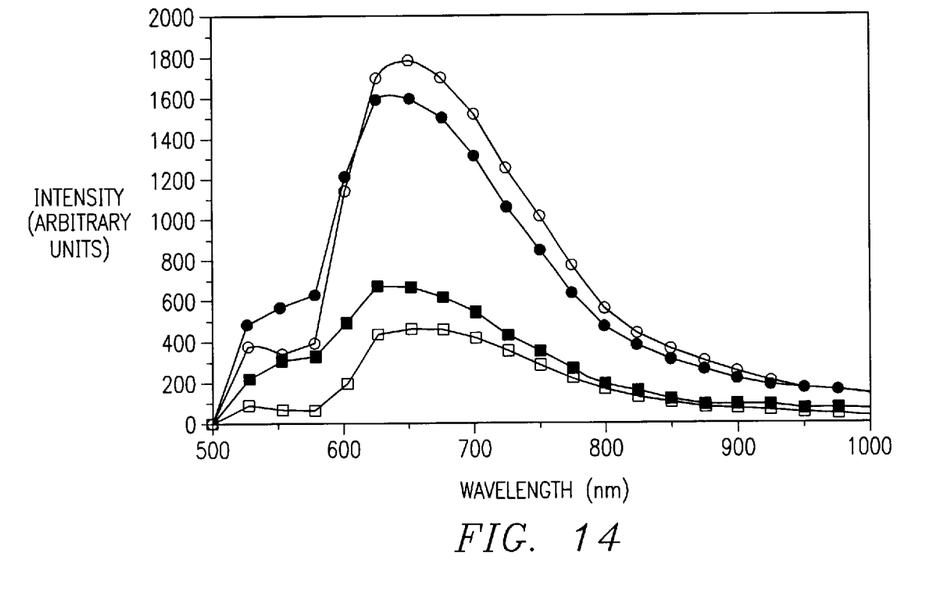
FIG. 14 illustrates reflectance measured from visually identified living gray and white matter in vivo.

To identify characteristic differences between gray and white matter, measurements were taken in another application of the disclosed device and method during three temporal lobectomies in humans performed for intractable epilepsy. These procedures entail removal of a portion of the temporal lobe, providing the opportunity of obtaining measurements from gray and white matter which are both clearly visible in the living resection bed (in vivo) and the resected specimen (ex vivo). A set of characteristic curves showing optical reflectance of gray and white matter were thereby obtained. FIG. 14 illustrates the characteristic reflectance difference between gray and white matter. The morphology of these curves between 500 and 600 nm was variable and did not reliably distinguish gray and white matter. However, the most distinguishable differences in reflectance spectra between gray and white matter are the slope of the curve between 700 and 850 nm and the maximum attained values. The maximum reflectance of white matter was greater than that of gray matter, and the curves for white matter had relatively steep slopes compared to those of gray matter. These data confirm that gray and white matter have different optical reflectances, with white matter yielding a stronger reflectance signal.

Monte-Carlo Computer Simulation

Although there are no theoretical or analytical solutions available to predict the experimental reflectance measurements from the NIR probe, Monte-Carlo simulations have been well accepted as a standard tool to produce computational predictions for light propagation in tissue computational studies using Monte-Carlo simulations to compare and confirm the experimental results. Detailed information about the simulation parameters and procedures has been described in the literature previously in Johns et al, 1998. The simulation code was provided by Wang et al, 1995 and Wang et al, 1997, which are incorporated herein by reference. The input parameters used for the simulations are as follows: the average index of refraction for tissues was 1.38, the mean cosine of the scattering angle for tissues was 0.9, and the tissue sample thickness was chosen as 10-cm, as described in Duck, 1990, incorporated herein by reference. The simulations were performed with a spatial step size of 0.05 mm and a maximum detection radius of 1.5 mm. The choice of input scattering and absorption coefficients was based on reported estimates by Zijlstra et al, 1991 and Hatcher et al, 1997, both of which are incorporated herein by reference, and parameter values were chosen to simulate brain tissue. Gray and white matter were simulated by having high and low absorption, respectively.

Figure 15:
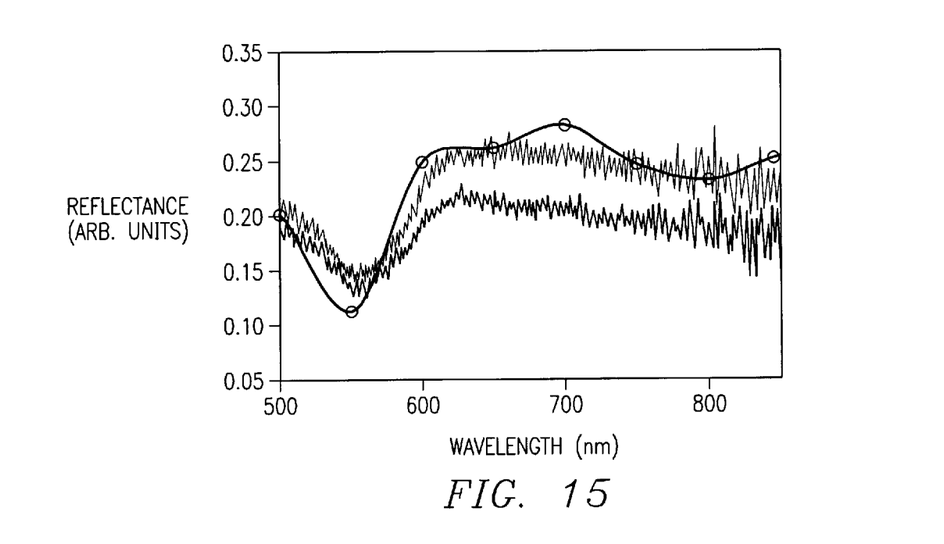
FIG. 15 illustrates a comparison of optical reflectance between the computer simulations and the in vivo measurement taken from 56 mm and 63 mm deep in the brain during neurosurgery.

Referring now to FIG. 15 there is illustrated data that exhibits a good correlation between the simulation and the reflectance measurements. The difference between these data and those shown in FIG. 2 is due to the addition of a calibration operation, in which signals derived from a calibration sample are subtracted from the data to eliminate the spectral effects from the light source, the fibers, and the instrument response.

Slope Algorithm

Examination of curves such as illustrated in FIG. 14 suggest that the slope of the curve in the 700 to 850 nm range might be used as a "summarizing index," with steep slopes being characteristic of white matter. To test the hypothesis that this slope index distinguishes white and gray matter, slopes were calculated for visually identified gray and white matter during the above lobectomy experiments. To minimize inter-patient variations, each slope was calculated relative to the slope derived from the gray matter 2 mm beneath the surface, i.e., each slope was divided by the slope value belonging to the measurement at a depth of 2 mm. This relative slope (RS) is dimensionless and can be used for comparison of data from different subjects. Furthermore, dividing by the reference slope in this fashion eliminates the spectral effects due to light source, fibers,. and instrument response so that no further calibration is necessary. Many data points are necessary to determine the slope, whereas only a few determine the maximal amplitude. The slope was therefore used rather than the maximum to reflect more general properties of the reflectance curve.

The RS values for visually identified gray and white matter in vivo were statistically different ($\alpha=0.05$, $p<0.001$). Gray matter taken in vivo has a mean RS value of 0.82 with a standard deviation (S.D.) of 0.23 and white matter has a mean RS value of 2.35 with a S.D. of 0.34. Similar results were seen from the ex vivo data ($0.82\pm0.27$ and $2.78\pm0.29$ for gray and white matter, respectively). The slope algorithm is straightforward, quick and yields a single number from the reflectance curve which distinguishes gray from white matter.

Rodent Model: Pilot Data

To assess the ability of the NIR probe to detect thin white matter lamina in an animal model, data were collected in the rodent. The rodent corpus callosum was used for this purpose, since it consists of a band of white matter with thickness from 0.3 to 0.75 mm, as described in Paxinos and Watson, 1986, as small or smaller than the thickness of found within the globus pallidus in humans, as described in Schaltenbrand et al, 1977. NMR measurements in the rodent can be directly compared to measurements of corpus callosum thickness made directly from subsequent histologic sections.

Figure 16A:
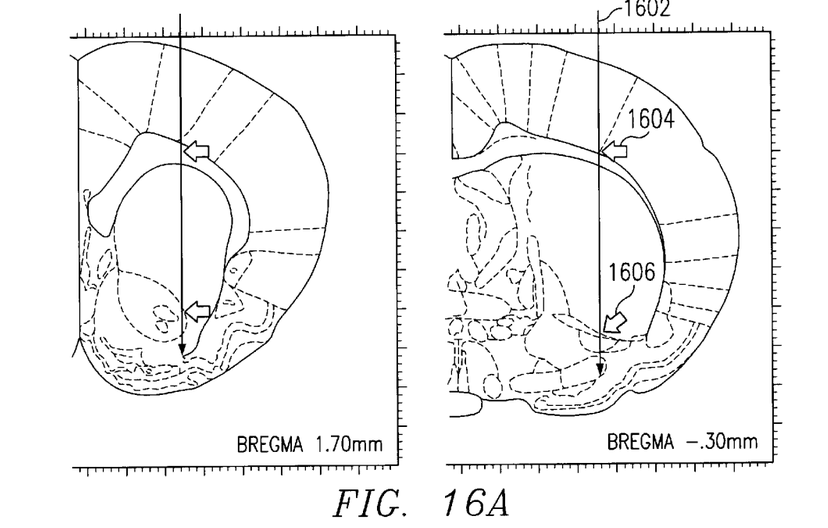
FIG. 16a illustrates two plates from a standard rodent atlas with NIR probe path superimposed to show thickness of corpus callosum in different coronal planes and proximity to anterior commissure.
Figure 16B:
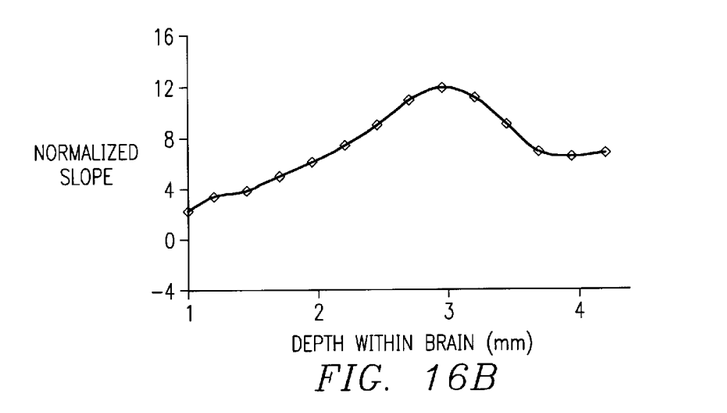
FIG. 16b is the relative slope vs, depth from rodent hemisphere.
Figure 16C:
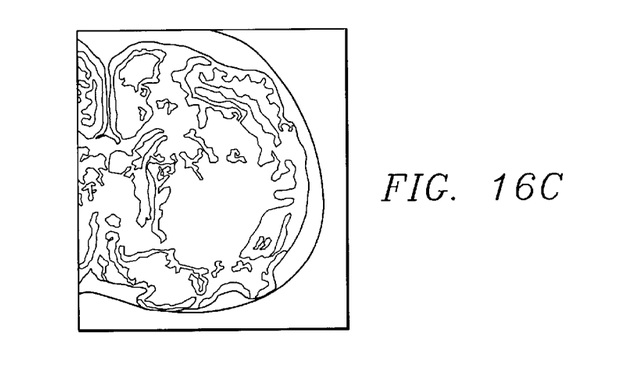
FIG. 16c is a histological section from the same rate indicating the deepest location of the probe track.

Sixteen NIR measurements were made at 0.25 mm intervals along a track 402 in an embodiment illustrated in FIG. 16A, in the anesthesized rat mounted in a stereotaxic apparatus (stereotaxic coordinates, anterior 1.7 mm from bregma, lateral 2.5 mm from the midline (according to the standard rat atlas, as described in Paxinos and Watson, 1986). The track 1602 was run in an anterior-posterior plane in which the corpus callosum at a point 1604 was approximately 0.5 mm thick in the atlas, and the caudate/putamen (striatum) is situated approximately 4.0 mm below the corpus callosum at a point 1606. A probe run along the track 1602 would be expected to give relatively low readings at depths of gray matter, a peak reading as the corpus callosum was traversed, and end with intermediate values since the rodent striatum is a mixture of gray with numerous white matter fascicles. FIG. 16B illustrates probe data indicating that this is exactly what was found, including the intermediate slope values found in striatal tissue. Note that high values of slope indicate white matter and low values indicate gray matter. The peak at 3 mm correlates to the depth of the midpoint of the corpus callosum. FIG. 16C illustrates the histologic section through the probe track. Notice that the tip of the probe descended to a depth of 3.0 mm below the cortical surface. Because of tissue shrinkage the "histological depth" is only 75% of the actual depth of the probe from cortical surface. Allowing for this shrinkage, the data indicate that the peak NIR probe value obtained at a depth of 3.0 mm corresponds to the localization of the corpus callosum in the histological section.

Stereotactic Procedures in Humans

The next set of experiments entailed the use of the probe during stereotactic surgeries in humans. The probe was placed in standard stereotactic apparatus (described in CRW, Radionics, Burlington, Mass.) and inserted by means of a hand micrometer into the brain with measurements obtained every 1 mm from the cortical surface to the stereotactic target. In four cases, measurements were obtained every 0.5 mm (the limits of the hand micrometer) for the deepest 2 to 3 cm. Slopes were calculated as above and normalized to the measurements obtained at 2 mm. The slope vs. depth graph was calculated and displayed in real time.

In the first five cases, the probe was only inserted 1.5 cm. Relative slope values from the first 5 to 8 mm were lower than those from deeper levels, corresponding to cortical gray matter lying superficial to white matter.

In the next nineteen patients, the NIR probe was inserted all the way to the final target with measurements taken serially as before. Reflectance vs. depth graphs were constructed and compared to imaging data as follows: for ablative lesions (thalamotomy and pallidotomy), postoperative MRI scans were obtained utilizing scan planes encompassing the entire probe track. Distances from the cortical surface to various structural boundaries could then be directly measured on the images and compared to peaks or troughs seen in the reflectance graph.

After DBS implantation, MRI scans were not available and these patients underwent a postoperative CT scan utilizing 1-mm thick axial slices. After correcting for the difference in angle between the CT scan plane and the probe path, the site of the electrode could be readily identified on each axial slice and the distance of this site from the cerebral surface along the electrode track could be calculated.

In three cases, an additional method was used. The MRI data set obtained preoperatively was imported into a workstation (described in Stealth, Sofamor-Danek) and oblique axial slices chosen identical to those of the CT scan. The position of the probe on each axial CT slice could then be immediately transferred to the MRI axial slice and from there to all three orthogonal planes within the workstation data set.

Imaging data were available for intraoperative use as well as for postoperative validation. This was accomplished by displaying an MRI or CT data set on a workstation in the operating room, and utilizing images angled to recreate the plane containing the proposed probe track. In this fashion, peaks and troughs in the reflectance graph could be compared to structures seen in these imaging studies to provide immediate validation.

Results of Deep Stereotactic Procedures

Figure 17:
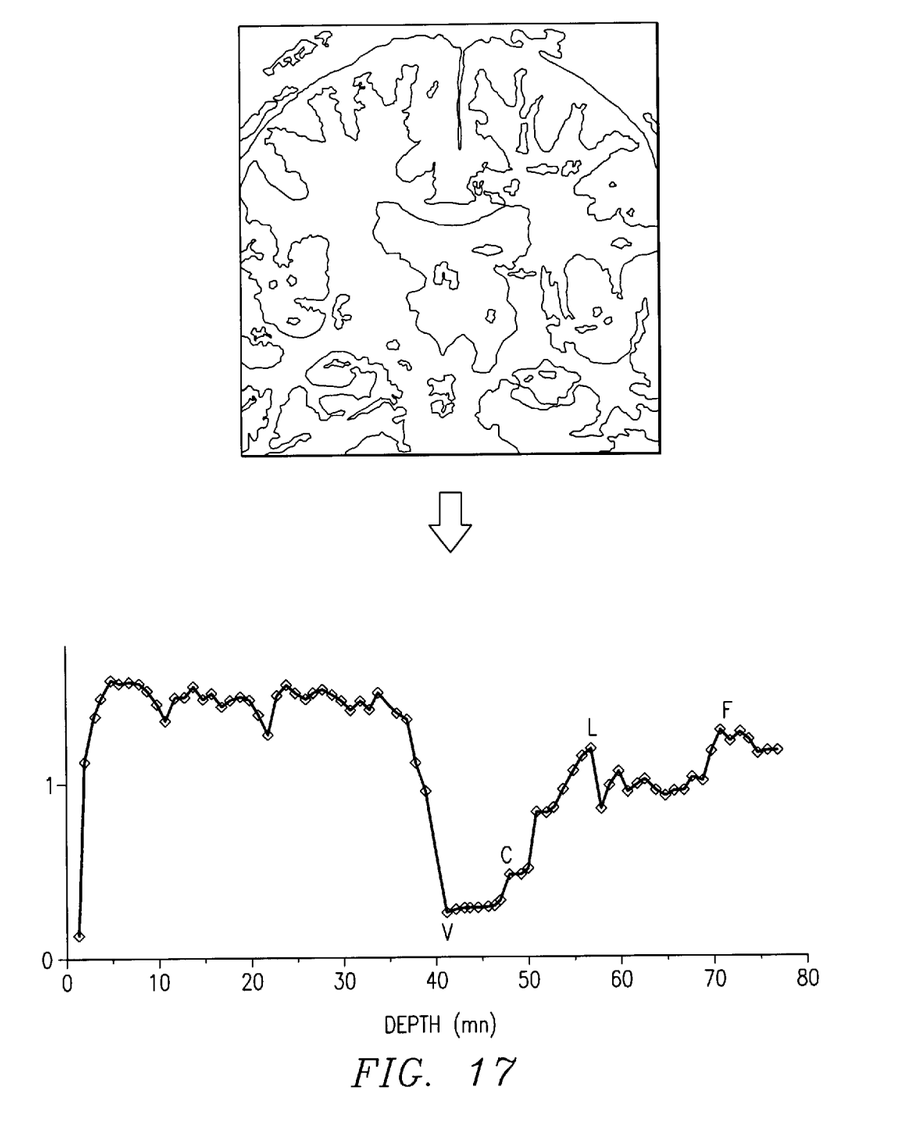
FIG. 17 illustrates a coronal MRI image after thalamotomy.

Method of Comparison of Images to NIR Graphs. The depths of each of the gray-white boundaries along the probe track were measured from the imaging studies, and these values used to mark the NIR graph. For example, in FIG. 17 the depth of the white matter lamina superior to the thalamus (marked "L" in the image) was measured from the cortical surface as 57 mm. The "L" on the graph was then placed at the site corresponding to 57 mm, and found to be coincident with a peak in the NIR signal. This peak then correlated with the lamina L. It is important to note that all our correlations were based on such measurements and not simply by labelling plausible peaks or troughs on the NIR graph.

Correlation to Imaging. The following is a summary of results from the first nineteen patients receiving NIR measurements from deep subcortical structures. The probe passed near sulci in ten of the nineteen patients. In all ten, troughs were seen in the NIR signal indicating nearby CSF within the sulcal space. A high "plateau" correlating with deep subcortical white matter was seen in all nineteen patients. Small areas of FLAIR or dark T1 signals appearing in the MRI studies just superolateral to the frontal horn produced troughs in the NIR signal in three patients. The ventricle was seen as a striking trough in the NMR signal in all thirteen patients in which the probe entered the ventricular system, and the width of the trough correlated to the physical length of the path through the ventricle. The caudate nucleus was seen as a trough in the NIR signal in all eleven cases in which the probe passed adjacent to this structure. A peak in the NIR signal corresponding to the white matter capsule covering the superior part of the thalamus was seen in all but one of the thalamotomies, and a plateau corresponding to the gray matter of the thalamus was seen in all thalamotomies.

The gray-white boundary between the internal capsule and putamen was seen in all five pallidotomies. Peaks correlating to the lamina between the putamen and the external segment of the globus pallidus were seen in three cases, and to the lamina between the external and internal segments of the globus pallidus in three cases. The white matter forming the floor of the globus pallidum was seen as an NMR peak in a trajectory directed slightly lateral to the GPi target, but was not clearly seen in the only other track that extended to this level. Whether the probe failed to detect the white matter of the floor or whether the floor consisted of a mixture of gray and white matter is unclear. Peaks corresponding to sites of previous lesions were seen in two trajectories, and one medially directed track through the internal capsule produced an NIR curve with white matter values only.

The above experimental results exhibit that the NIR probe can distinguish layers of gray and white matter as thin as 1 mm. However, the limits of its resolution and the ability to distinguish the fine layers at the base of the basal ganglia, important during DBS localization, have yet to be established.

SPECIFIC METHODS

This section describes the methods used to obtain the supporting data to the process and apparatus described hereinabove.

1. Rodent Surgery and Stereotaxic Procedure

Male Sprague-Dawley rats (200–250 g) are anesthetized with Nembutal (60 mg/kg, i.p.) and mounted in a Kopf stereotaxic apparatus. Local anesthetic (Lidocaine, 2%) is injected at pressure points above ear canals, and into wound margin in the scalp incision. The periosteum is then removed and a hole drilled in the skull above the probe implantation coordinates. The dura is then lanced and the probe/microelectrode placed at the top of the cortex. The surface of the cortex is defined as "0" on the microdrive, and all measurements taken from this point. After data collection, the skin is then sutured and treated with antibiotic cream. The animal is then removed from the stereotaxic apparatus and kept warm with a heat lamp until it regained normal body movements.

2. Rodent Neurohistology

The day after surgery, the rats are injected with a lethal dose of Nembutal (120 mg/kg, i.p.). After the animal is dead, the dorsal surface of the skull is removed and the head removed and placed in 10% neutral buffered formalin solution for 2 days. Next, the head is mounted in the stereotaxic apparatus and a knife blade mounted in the stereotaxic holder. A coronal knife cut is made in the same plane as the probe track, with the cut at the level of the hypothalamus. The brain is removed and placed in 10% neutral buffered formalin containing 20% sucrose. Once the brain has "sunk" (usually within 24 hrs.), coronal sections are cut on a freezing microtome at 40 mm thickness. Sections through the probe track are mounted on subbed slides, stained with Cresyl Violet and coverslipped.

3. Measurement of Histological Distances in Rodents

Computer imaging procedures are used to measure the distance from the cortical surface to the maximum extent of the NIR Probe track. Because the probe is so large it leaves a clear lesion. Using NeuroLucida software (MicroBrightField, Inc.), the outline of the tissue section is drawn, the outline of the corpus callosum and the deepest point of the probe track indicated. The depth of the probe track from cortical surface is measured to the nearest 0.1-mm. The maximum depth is used to calculate the "percent depth" measurements for all points where NIR measurements are taken (e.g., at 0.1 mm intervals). To be certain that the greatest depth of the probe is reflected by the tissue damage caused by the probe, in five animals a microlesion is made with the microelectrode that is within the NIR-probe. If it is found that the microlesion is at the same depth as the damage caused by the probe tip (e.g., see FIG. 16B), then use of the microlesion for the remainder of the experiments would be terminated and reliance would be upon the damage caused by the probe tip to mark the maximal depth of the track.

4. Measurements of Distance From Images

All images are viewed with the Stealth workstation or are scanned into computr format (TIFF) to be viewed on a standard computer screen with imaging software (Photoshop, Adobe). On the Stealth workstation, distance measurementst of the standard software. For the scanned images, we will use the length scale provided with each MRI and CT image. Measurements of distance between two points in pixels is allowed by software and can be converted to mm or cm by comparison with this scale. Experience with the magnification factors offered by these software packages verifies that measurements below 1-mm are readily attainable.

5. Microelectrode Recording.

MER techniques are now standard and complete equipment packages are commercially available. Established protocols are adhered to for recordings in human (Lozano et al, 1996; Vitek et al, 1998) and primate brain (Fetz et al, 1976; German et al, 1976) to distinguish areas identified as gray matter by the presence of single cell recordings, and as white matter identified by areas of silence. In both human and rodents, Frederick Haer tungsten microelectrodes are used, with an impedance of 1.21–1.5 megohms (tested with a Winston Impedance Meter). In the rodent, recordings use a Grass P511 preamplifier with signals fed into a Hewlett Packard oscilloscope and Grass Audio amplifier. A Trent-Wells microdrive hydraulically advances the microelectrode and units are recorded beginning at the cortical surface to the depth of the recording track (depending upon the stereotaxic location either 3.0 or 8.0 mm). Areas of white matter are defined as regions in which there is no single unit activity (e.g., when in the corpus callosum). Similar procedures are used in recording from man, except we will use electrophysiological equipment from Axon Instruments (Guideline System 3000). Electrophysiological noise has been successfully suppressed using the Hum Bug from Quest Scientific, Inc. Examples of single unit recording in a human is illustrated in FIG. 18.

The microelectrode recordings in humans are interpreted according to established protocols (Lozano et al, 1996; Vitek et al, 1998). Gray matter is identified by single cell signals and white matter by areas of silence. Maps of gray and white matter along the track can thereby be constructed,(see FIG. 17).

6. Human NIR Measurements.

After placement of the stereotactic frame, the choice of target is made with combined CT and MRI imaging, using a protocol described previously for thalamic and pallidal targets (Giller et al, 1998). A burrhole is made under local anesthesia with sedation and corticotomy made for entrance of the probe. The NIRIER or NIR probe with side sensors are held in the hydraulic microdrive provided with the NMER equipment (Guideline System 3000, Axon Instruments, Foster City, Calif.). As described in Preliminary Studies, each relative slope value derived from a reflectance curve is normalized by dividing by the relative slope value obtained at 2 mm. The resulting data are plotted against depth.

7. Imaging Procedures.

MRI: MRI studies are obtained on the 1.5 tesla Phillips Gyroscan at our institution. An inversion recovery type sequence is used (TR=1350 ms, TI=300 ms, TE=30 ms, 20 cm field of view) to obtain 2 mm axial and coronal slices. This sequence is well suited for gray-white discrimination, especially when viewed with video reversal. Preoperative images include oblique axial planes coinciding with the AC-PC plane, and postoperative images (for those patients receiving ablative surgery) will include these same axial planes as well as oblique coronal planes containing the entire probe track. The images are imported into a Stealth workstation (Stealth, Sofamor-Danek) or converted into computer image files.

CT:CT studies are obtained with a GE High Speed Advantage device. Preoperative scans are obtained according to our established operative protocol (Giller et al,1998), and postoperative scans are obtained with 1-mm thickness.

8. Imaging Protocols a. Preoperative Imaging.

Pre-operative MRI scans are obtained and loaded into a workstation (Stealth, Sofamor-Danek) for display in the operating room during stereotactic procedures. The software allows display of the single reconstructed oblique coronal plane containing the entire probe track from burrhole to target. The burrhole site is chosen on the MRI images based on distances from midline and coronal suture measured from the actual burrhole. The target is chosen on the MRI images to coincide with the target chosen for surgery. Depths beneath the cerebral surface are then measured directly on the display and compared to transition points in the NIR and MER data.

b. Postoperative Imaging.

The available post-operative imaging differs for ablative procedures and for DBS implantation, and these cases must be considered separately.

Ablative Lesions: MRI scans are obtained (inversion recovery) post-operatively with oblique coronal views containing the entire track either directly if the track is visible or by containing the burr hole and lesion otherwise. Analysis will then proceed as for the pre-operative imaging data set.

DBS: In general, only CT images are available at our institution after DBS implantation due to safety concerns regarding MRI scans of patients with implants. CT scans of 1-mm thickness is obtained and the probe position on each slice identified. This position is then determined on the MRI axial images as follows. Oblique axial images in the MRI data set are selected with the Stealth workstation to approximate the postoperative axial CT slices emulating the gyral and sucal patterns seen on the CT images. The position of the probe on each axial CT slice can then be directly identified on the MRI axial slice, and from there be identified in the reconstructed coronal planes which best allow identification of subcortical structures. These locations can then be matched to the peaks and transitions seen in the NIR graphs.

9. Comparison of Time Required

The time taken for NIR measurements every 1-mm along a track is well established (approximately 86 seconds per centimeter). The time required for MER can therefore be calculated as the time taken for a track using NMR only subtracted from the total time taken for a track using simultaneous NIR and MER measurements. The time required for delays will also be added to the total time for each modality. A difference of 10 minutes per track is considered clinically significant, since this would produce a difference of 20 to 30 minutes for protocols using 2 or 3 tracks. Statistical Significance is evaluated by paired t-test. Time will only be estimated for the end-sensor probe.

Although the preferred embodiment has been described in detail, it should be understood that various changes, substitutions and alterations can be made therein without departing from the spirit and scope of the invention as defined by the appended claims.

Appendix

The following references have been cited hereinabove, all of which are incorporated herein by reference:

Albe-Fessard D, Arfel G, Guiot G, Hardy J V G, Hertzog E, Aleonard P, Derome P. *Derivations d'activites spontanees et evoquees dans les structures cerebrales profondes de l'homme.* Rev Neurol 1962;106:89–105.

Alexander E I, Kooy H M, van Herk M, Schwartz M, Barnes P D, Tarbell N, Mulkern R V, Holupka E J, Loeffler J S. *Magnetic resonance image-directed stereotactic neurosurgery: Use of image fusion with computerized tomography to enhance spatial accuracy.* J Neurosurg 1995;83:271–276.

Alterman R L, Sterio D, Beric A, Kelly P J. *Microelectrode recording during posteroventral pallidotomy: impact on target selection and complications.* Neurosurgery 1999;44:315–323.

Baron M S, Vitek J L, Bakay R A E, etal. *Treatment of advanced Parkinson's diseae by GPi pallidotomuy: 1-year results of a pilot study.* Ann Neurol 1996;40:355–366.

Bevilacqua, F. *Local optical characterization of biological tissues in vitro and in vivo.* PhD Dissertation. Swiss Federal Institute of Technology, Lausanne. 1998. Bevilacqua F, Piguet D, Marguet P, Gross J D, Jakubowski W, Venugopalan V, Tromberg B J, Depeursinge C. *Superficial tissue optical property determination using spatially resolved measurements close to the source: comparison with frequency domain photon migration measurements.* SPIE Proceedings 1999;3597:540–547.

Burchiel, K. Comment. Neurosurgery 42, 64–65. 1998. Burchiel K, Nguyen T T, Coombs B D, Szumoski J. MRI *distortion and stereotactic neurosurgery using the Cosman-Roberts-Wells and Leksellframes.* Stereotact Funct Neurosurg 1996;66:123–136.

Cheong W F, Prahl A, Welch A J. *A review of the optical properties of biological tissues.* IEEE J Quantum Electronics 1990;26:2166–2185.

Dewey R B, Giller C A, Broline S K, Mendelsohn D B, Lacritz L H, Cullum C M. *Clinical outcome of unilateral pallidotomy without microelectrode recording for intractable Parkinson's disease.* Parkinson's and Related Disorders 2000;6:7–16.

Dogali M, Fazzini E, Kolodny E, Eidelberg D, Sterio D, Devinsky O, Beric A. *Stereotactic ventral pallidotomy for Parkinson's disease.* Neurology 1995;45:753–761.

Duck F A. *Physical Properties of Tissue: A Comprehensive Reference Book.* San Diego, Calif.:Academic Press, 1990:

Fetz E, Cheney P D, Germnan D C. *Corticomotoneuronal connections of precentral cells detected by post-spike averages of EMG activity in behaving monkeys.* Brain Res 1976;114:505–510.

German D C, Fetz E. *Responses of primate locus coeruleus and subcoeruleus neurons to stimulation at reinforcing brain sites and to natural reinforcers.* Brain Res 1976;109:497–514.

Giller C A, Dewey R B, Ginsburg M I, Mendelsohn D B, Berk A M. *Stereotactic pallidotomy and thalamotony using individual variations of anatomic landmarks for localization.* Neurosurgery 1998;42:56–62.

Gillingham F J, Watson W S, Donaldson A A, Naughton J A L. *The surgical treatment of parkinsonism.* Br Med J 1960;2:1395–1402.

Gross R E, Lombardi W J, Hutchison W D, Narula S, Saint-Cyr J A, Dostrovsky J O, Tasker R R, Lang A E, Lozano A M. *Variability in lesion location after microelectrode-guided pallidotomy for Parkinson's disease:anatomical, physiological, and technicalfactors that determine lision distribution.* J Neurosurg 1999;90:468–477.

Hanley J A, McNeil B J. *The meaning and use of the area under a receiver operating characteristic (ROC) curve.* Radiology 1982;143:29–36.

Heilbrun M P, Koehler S, McDonald P, Faour F. *Optimal target localization for ventroposterolateral pallidotomy; the role of imaging, impedance measurement, macrostimulation and microelectrode recording.* Stereotact Funct Neurosurg 1997;69:19–27.

Hielscher A H, Liu H, Chance B, Tittel F K, Jacques S L. *Time resolved photon emissionfrom layered turbid media.* Appl Optics 1996;35:719–728.

Jankovic J, Cardoso F, Grossman R G, Hamilton W J. *Outcome after stereotactic thalamotomy for parkinsonian, essential, and other types of tremor.* Neurosurgery 1995;37:680–686.

Johns, M. *Development of Fiber Optic Probe to Obtain Optical Reflectance of Human Brain Tissue In Vivo.* 1997. Master's Thesis. University of Arlington and University of Texas Southwestern Medical Center at Dallas.

Johns M, Giller C A, Liu H. *Computational and in vivo investigation of optical refelectance from human brain to assist neurosurgery.* J Biomedical Optics 1998;3:437–445.

Kelly P J, Derome P, Guiot G. *Thalamic spatial variability and the surgical results of lesions placed with neurophysiologic control.* Surg Neurol 1978;9:307–315.

Kishore A, Turnbull I M, Snow B J, de la Fuente-Fernandez R, Schulzer M, Mak E, Yardley S, Calne D B. *Efficacy, stability and predictors of outcome of pallidotomy for Parkinson's disease. Six-month follow-up with additional 1-year observations.* Brain 1997;120:729–737.

Laitinen L V, Bergenheim A T, Hariz M I. *Leksell's posteroventral pallidotomy in the treatment of Parkinson's disease.* J Neurosurg 1992;76:53–61.

Laitinen L V, Johansson G G, Sipponen P. *Impedance and phase angle as a locating method in human stereotaxic surgery.* J Neurosurg 1966;25:628–633.

Lang A E, Lozano A M, Montgomery E, Duff J, Tasker R, Hutchinson W. *Posteroventral medial pallidotomy in advanced Parkinson's disease.* N Engl J Med 1997;337:1036–1042.

Linazasoro G, Guridi J, Gorsope A, Ramos E, Mozo A, Obeso J A. *Posteroventral pallidotomy in Parkinson's disease: Clinical results in 27 patients.* Mov Disord 1996;11:240

Liu H, Hielscher A H, Tittel F K, Jacques S L, Chance B. *Influence of blood vessels on the measurement of hemoglobin oxygenation as determined by time-resolved reflectance spectroscopy.* Medical Physics 1995;22:1209–1217.

Liu H, Miwa M, Beauvoit B, Wang N G, Chance B. *Characterization of absorption and scattering properties of small-volume biological samples using time-resolved spectroscopy.* Analytical Biochemistry 1993;213:378–385.

Lozano A M, Hutchinson W, Kiss Z, Tasker R T, Davis K, Dostrovsky J. *Methods for microelectrode-guided posteroventral pallidotomy.* J Neurosurg 1996;84:194–202.

Lozano A M, Lang A E, Galvez-Jimenez N, Miyasaki J, Duff J, Hutchinson W D, Dostrovsky J O. *Effect of GPi pallidotomy on motorfiinction in Parkinson's disease.* Lancet 1995;346:1383–1387.

Matcher S J, Cope M, Delpy D T. *In vivo measurements of the wavelength dependence of tissue-scattering coefficients between 760 and 900 nm measured with time resolved spectroscopy.* Appl Optics 1997;36:386–396.

Mayeux R, Denaro J, Hemenegildo N, Marder K, Tang M X, Cote L J, Stern Y. *A population-based investigation of Pardinson's disease: Relationship to age and gender.* Arch Neurol 1992;49:492–497.

Mourant J R, Johnson T M, Los G, Bigio I J. *Non-invasive measurement of chemotherapy drug concentrations in tissue: preliminary demonstration of in vivo measurements.* Phy Med Biol 1999;44:1397–1417.

Okada E, Firbank M, Schweiger M, Arridge M, Cope, Delpy D T. *Theoretical and experimental investigation of near-infrared light propagation in a model of the adult head.* Applied Optics 1997;36:21–31.

Patterson M S, Chance B, Wilson B C. *Time resolved reflectance and transmittance for the non-invasive measurement of tissue optical properties.* Appl Optics 1989;28:2331–2336.

Paxinos G, Watson C. *The Rat Brain in Stereotaxic Coordinates.* New York:Academic Press, 1986:

Robinson B, Bryan J S, Rosvold H E. *Locating brain structures.* Arch Neurol 1965;13:477–486.

Samuel M, Caputo E, Brooks D J S A, Scaravilli T, Branston N M, Rothwell J C, Marsden C D, Thomas D G L A J, Quinn N P. *A study of medial pallidotomy for Parkinson's disease: clinical outcome, MRI location and complications.* Brain 1998;121:59–75.

Schaltenbrand G, Wahren W. *Atlas for Stereotaxy of the Human Brain.* Second ed. Stuttgart:Thieme, 1977:

Scott R, Gregory R, Hines N, Carroll C, Hyman N, Papanasstasiou V, Leather C, Rowe J, Silburn P, Aziz T. *Neuropsychological, neurological and functional outcome followinng pallidotomy for Parkinson's disease. A consecutive series of eight simultaneous bilateral and twelve unilateral procedures.* Brain 1998;121:659–675.

Shannon K M, Penn R D, Kroin J S A C H, Janko K A, York M, Cox S J. *Stereotactic pallidotomy for the treatment of Parkinson's disease. Efficacy and adverse effects at 6 months in 26 patients.* Neurology 1998;50:434–438.

Starr P A, Kelly P J, Burchiel K. *Axon Guideline System 3000.* Neurosurgery 1999a;44:1354–1357.

Starr P A, Vitek J L, DeLong M, Bakay R A E. *Magnetic resonance imaging-based stereotactic localization of the globus pallidus and subthalamic nucleus.* Neurosurgery 1999b;44:303–314.

Sutton J P, Couldwell W, Lew M F, Mallory L, Grafton S, DeGiorgio C, Welsh M, Apuzzo M U, Ahmadi J, Waters C H. *Ventroposterior medial pallidotomy in patients with advanced Parkinson's disease.* Neurosurgery 1995;36:1112–1117.

Taha J M, Favre J, Baumann T K, Burchiel K J. *Functional anatomy of the pallidal base in Parkinson's disease.* Neurosurgery 1996;39:1164–1168.

Tanner C M, Hubble J P, Chan P. *Epidemiology and genetics of Parkinson's disease.* In: Watts R L, Koller W C, eds. *Movement Disorders: Neurologic Principles and Practice.* New York: McGraw-Hill, 1997:137–152.

van der Zee, P., Esserpreis, M., and Delpy, D. T. *Optical properties of brain tissue.* SPIE. 1992.
Ref Type: Conference Proceeding Vitek J L, Bakay RAE, Hashimoto T, Kaneoke Y, Mewes K, Zhang J Y, Rye D, Starr P A, Baron M, Turner R, DeLong M. *Microelectrode-guided pallidotomy: technical approach and its application in medically intractable Parkinson's disease.* J Neurosurg 1998;88:1027–1043.

Wang L H, Jacques S L, Zheng L Q. MCML—*Monte Carlo modeling of photon transport in multi-layered tissues.* Computer Methods and Programs in Biomedicine 1995;47:131–146.

Wang L H, Jacques S L, Zheng L Q. CONV—*convolution for responses to a finite diameter photon beam incident on multi-layered tissues.* Computer Methods and Programs in Biomedicine 1997;54:141–150.

Zijlstra W G, Buursma A, Meeuwsen-van der Roest W P. *Absorption spectra of human fetal and adult oxyhemoglobin, de-oxyhemoglobin, carboxyhemoglobin and methemoglobin.* Clinical Chemistry 1991;37:1633–1638.

What is claimed is:

1. A method for determining the insertion point for an object at a desired location within tissue of varying types, comprising the steps of:
    measuring parameters of tissue at an entry point in the tissue;
    periodically measuring the parameters of the tissue along a line extending from an entry point and moving away therefrom;
    determining if at least one boundary between tissues has occurred during the measurement process;
    comparing the measurements along the line to a predetermined map of the tissue boundaries; and
    selecting a point on the map corresponding to the desired location within the tissue when the measured parameters indicate that the measurements are taking place in proximity to the desired location.

2. The method of claim 1, wherein the step of measuring comprises measuring reflectance properties of the tissue.

3. The method of claim 2, wherein the step of measuring the reflectance properties comprises measuring the local reflected properties.

4. The method of claim 2, wherein the step of measuring the reflectance properties of the tissue comprises disposing an emitter and detector in close proximity to each other on the end of a probe wherein the probe is inserted into the entry point and moved along the line with radiation emitted form the emitter and detected at the detector.

5. The method of claim 4, wherein the step of periodically measuring comprises moving the probe along the line from the insertion point inward along the line from the entry point inward away from the entry point.

6. The method of claim 1, wherein the step of measuring comprises continuously measuring.

7. The method of claim 1, and further comprising the step of inserting the object into the tissue along the line and to a depth equal to the depth where the measurement corresponds to the selection point.

8. A system for determining the insertion point for an object at a desired location within tissue of varying types, comprising:
    a measurement device for measuring parameters of tissue;
    a motive device for moving said measurement device along a desired path from an entry point in the tissue along a line extending from an entry point and moving away therefrom;
    said measurement device periodically measuring the parameters of the tissue as said measurement device is moved along said line;
    an analysis system for determining if at least one boundary between tissues has occurred during the measurement process;
    said analysis system comparing the measurements along said line to a predetermined map of the tissue boundaries; and
    said analysis system selecting a point on the map corresponding to the desired location within the tissue when the measured parameters indicate that the measurements are taking place in proximity to the desired location.

9. The system of claim 8, wherein the said measurement device is operable to measure reflectance properties of the tissue.

10. The system of claim 2, wherein the step of measuring the reflectance properties comprises measuring the local reflectance properties.

11. The system of claim 10, wherein the said measurement device comprises an emitter and detector disposed in close proximity to each other on the end of a probe wherein said probe is inserted into the entry point and moved along said line with radiation emitted form said emitter and detected at said detector.

12. The system of claim 11, wherein the said motive device is operable to move said probe along said line from the insertion point inward along said line from the entry point inward away from the entry point.

13. The system of claim 8, wherein said measurement device is operable to continuously measure.

* * * * *